Sept. 27, 1955 F. W. ANDERSON Plant Pat. 1,421

NECTARINE TREE

Filed Jan. 14, 1955

WITNESS

Addison E. Avery

INVENTOR

Frederic W. Anderson

Webster & Webster

ATTYS.

United States Patent Office

Plant Pat. 1,421
Patented Sept. 27, 1955

1,421

NECTARINE TREE

Frederic W. Anderson, Merced, Calif.

Application January 14, 1955, Serial No. 481,983

1 Claim. (Cl. 47—62)

This invention relates to a new and distinct variety of nectarine tree which bears medium sized, highly colored, substantially white fleshed fruit having good shipping and eating qualities.

As compared to the John Rivers nectarine (unpatented), and which is presently the leading nectarine in acreage in California, the fruit of the instant variety ripens at approximately the same time but is larger in size; has more exterior red color; has a much shorter chilling requirement; and is firmer in flesh, remaining firm and marketable over a considerably longer period of time.

Additionally, the present variety of nectarine tree is a more regular bearer and a heavier producer than said John Rivers nectarine.

The present variety—taking into consideration its good shipping and eating qualities, and the advantageous distinctive characteristics, as above, in comparison to the John Rivers nectarine—appears to have greater commercial potential.

The present variety of nectarine tree was originated by me—during the course of a continuing program seeking more desirable commercial nectarines—in my experimental orchard at Le Grand, Merced County, California, as an F–2 cross of the Le Grand nectarine (United States Plant Patent No. 549), and the John Rivers nectarine (unpatented).

After origination of the cross, and when it came into bearing, it was recognized as having the distinctive characteristics—as herein described—which made it commercially desirable, and the variety was therefore selected for subsequent reproduction.

Asexual reproduction of the variety was accomplished by me in my experimental nursery, as aforesaid; such reproduction being accomplished by top-working—specifically by budding—on mature orchard trees. These asexual reproductions were found to carry forward all of the characteristics of the parent, particularly those which distinguish the variety from the John Rivers nectarine.

Figure 1:
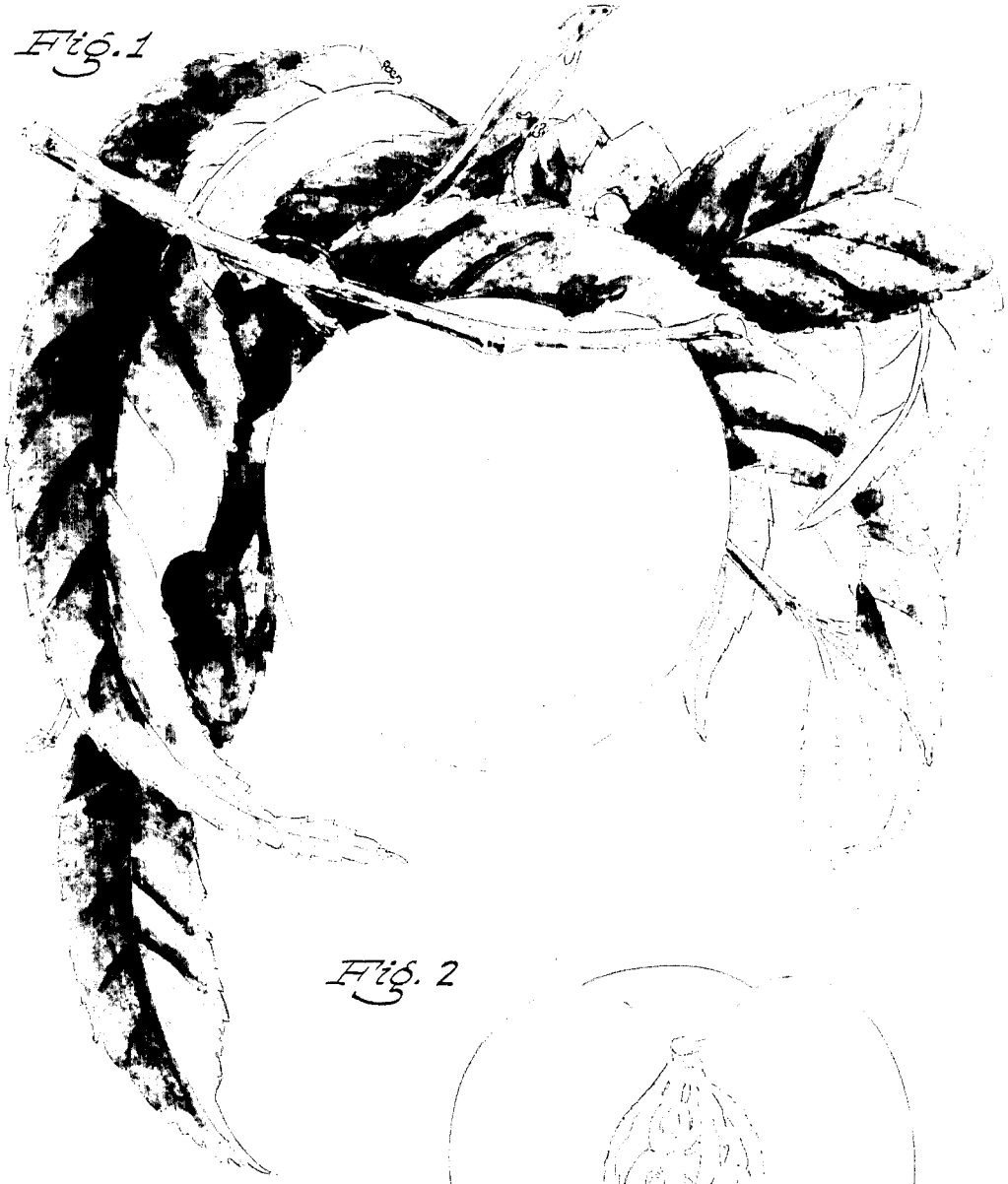
Fig. 1 is a perspective view of the fruit, together with a twig and leaves of the present variety.
Figure 2:
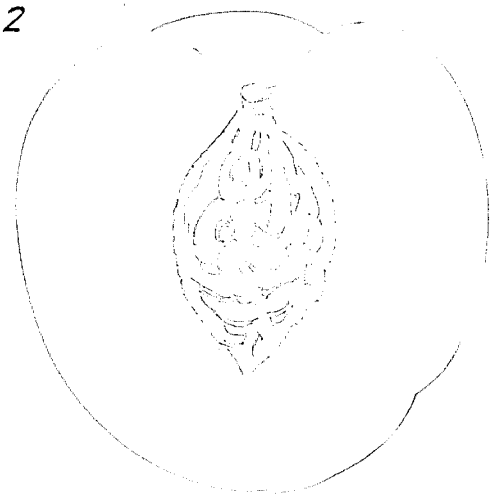
Fig. 2 is a sectional elevation of the fruit with the stone exposed.
Figure 3:
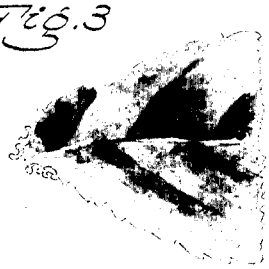
Fig. 3 is a fragmentary sectional elevation of one of the leaves showing particularly the glands.

Referring now more specifically to the pomological details of this new and distinct variety of nectarine tree, the following is an outline description thereof; all major color plate identifications being by reference to Maerz and Paul Dictionary of Color:

Tree:
- *Size.*—Medium.
- *Vigor.*—Medium.
- *Growth.*—Upright to spreading.
- *Density.*—Open.

- *Production.*—Very productive.
- *Bearing.*—Regular bearer.

Trunk:
- *Size.*—Medium.
- *Surface.*—Medium.

Branches:
- *Size.*—Medium.
- *Surface.*—Medium.
- *Lenticels.*—Medium number; medium size.

Leaves:
- *Size.*—Medium. Average length—6¼"; average width—1 7/16".
- *Thickness.*—Medium.
- *Margin.*—Crenate.
- *Petiole.*—Medium length; medium thickness.
- *Glands.*—Average number—three. Reniform. Position—usually two on petiole and one or more on blade.
- *Stipules.*—None.
- *Color.*—Top side—medium green (22–L–7). Under side—lighter green (20–K–6), with a still lighter green (17–J–2) midrib.

Flower buds:
- *Size.*—Medium.
- *Form.*—Conic.

Flowers:
- *Blooming period.*—First and full, about with the July Elberta Peach (United States Plant Patent No. 15). Early to medium compared with other varieties.
- *Size.*—Large.

Fruit:
- *Date of first picking.*—June 18, 1954.
- *Date of last picking.*—June 28, 1954.
- *Maturity when described.*—Eating ripe.
- *Size.*—Uniform; medium. Average diameter axially—2½". Average transversely in suture plane—2½".
- *Form.*—Uniform; symmetrical; globose.
- *Suture.*—Distinct; shallow. Slight depression beyond pistil point.
- *Ventral surface.*—Rounded slightly; strongly lipped.
- *Cavity.*—Rounded. Elongated in suture plane with suture showing on one side. Average depth—⅜". Average breadth—½".
- *Base.*—Rounded.
- *Apex.*—Short.
- *Pistil point.*—Apical.

Skin:
- *Texture.*—Medium thick; medium tender; free.
- *Tendency to crack.*—None.
- *Down.*—Wanting.
- *Color.*—Yellow (10–K–3), shading to a greenish yellow (12–L–2), overspread to a great extent with a dull red or rose (2–F–11 shading to 3–L–3).

Flesh:
- *Amygdalin.*—Moderate.
- *Juice.*—Moderate; rich.
- *Texture.*—Medium firm; melting.
- *Fibers.*—Few.
- *Ripens.*—Even.
- *Flavor.*—Subacid; vinous.
- *Aroma.*—Pronounced.
- *Eating quality.*—Good to best.
- *Color.*—Substantially white (9–B–1), with very light greenish mottling (17–D–1).
- *Surface of pit cavity.*—White, with a small area of pink (2–J–4) extending into the flesh from the apex of the stone.

Stone:
- *Type.*—Free. Parts from flesh smoothly.
- *Size.*—Medium. Average length—1 3/16"; average breadth—1 1/16"; average thickness—13/16".

*Form.*—Oblong.
*Base.*—Straight.
*Hilum.*—Oblong.
*Apex.*—Rounded.
*Sides.*—Equal.
*Ridges.*—Rounded.
*Pits.*—Elongated.
*Ventral edge.*—Thick.
*Dorsal edge.*—Full, with broad groove.
*Color.*—Tan (9–D–5 shading to 10–G–8).

Use: Market; local and long distance shipping; dessert.
Keeping quality: Medium.
Shipping quality: Good.

The tree and its fruit herein described may vary in slight detail due to climatic and soil conditions under which the variety may be grown.

The following is claimed:

A new and distinct variety of nectarine tree, as illustrated and described, characterized by medium sized, white fleshed, highly red colored, freestone fruit which ripens at approximately the same time as the John Rivers nectarine, but in comparison with the latter being a more regular bearer, a heavier producer, and the fruit having more exterior red color, a much shorter chilling requirement, being of larger size, firmer in flesh, and remaining firm and marketable over a considerably longer period of time.

No references cited.